United States Patent
Bachur, Jr.

(10) Patent No.: US 7,846,394 B2
(45) Date of Patent: Dec. 7, 2010

(54) APPARATUS AND METHOD FOR SEPARATING PARTICLES WITHIN A SPECIMEN

(75) Inventor: Nicholas R. Bachur, Jr., Monkton, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 674 days.

(21) Appl. No.: 11/865,756

(22) Filed: Oct. 2, 2007

(65) Prior Publication Data
US 2009/0084737 A1    Apr. 2, 2009

(51) Int. Cl.
*B01D 21/26* (2006.01)
*B01L 99/00* (2010.01)
*G01N 35/00* (2006.01)
*B07B 1/22* (2006.01)
*B01D 33/00* (2006.01)

(52) U.S. Cl. ............. 422/101; 210/787; 210/359; 436/45; 422/44; 209/278; 209/288

(58) Field of Classification Search ......... 210/787
See application file for complete search history.

(56) References Cited

U.S. PATENT DOCUMENTS

| | | |
|---|---|---|
| 4,037,723 A | 7/1977 | Wahl et al. |
| 4,683,058 A | 7/1987 | Lyman et al. |
| 5,887,725 A | 3/1999 | Tominaga et al. |
| 6,221,655 B1 | 4/2001 | Fung et al. |
| 2004/0116686 A1* | 6/2004 | Akashi et al. .......... 536/25.4 |
| 2006/0090430 A1 | 5/2006 | Trautman et al. |
| 2006/0278588 A1* | 12/2006 | Woodell-May .......... 210/787 |
| 2009/0129976 A1* | 5/2009 | Hoshino et al. .......... 422/44 |
| 2009/0218277 A1* | 9/2009 | Min et al. .......... 210/512.1 |
| 2010/0038244 A1* | 2/2010 | Wood et al. .......... 204/468 |

FOREIGN PATENT DOCUMENTS

| | | |
|---|---|---|
| WO | WO 99/58221 | 11/1999 |
| WO | WO 2004/105966 A1 | 12/2004 |
| WO | WO 2005/014772 A1 | 2/2005 |

* cited by examiner

*Primary Examiner*—Jill Warden
*Assistant Examiner*—Jennifer Wecker

(57) ABSTRACT

Embodiments of the present invention provide an apparatus and a method for separating particles within a sample. The apparatus includes a reservoir for receiving a biological specimen therein, wherein the specimen includes a plurality of different sized particles in a liquid. At least one physical state of the specimen is capable of being controlled in order to initially separate at least a first type of particles under the influence of gravity. The apparatus also includes a rotatable disk positioned proximate to the reservoir and configured to receive the first type of particles thereon. The disk has holes defined therethrough that are configured to further separate the first type of particles based on particle size. The apparatus includes a mechanism configured to rotate the disk, and at least one collection tube positioned proximate to the disk and configured to receive at least a portion of the first type of particles passing through respective holes defined in the disk and/or around the disk in response to rotation of the disk.

24 Claims, 2 Drawing Sheets

APPARATUS AND METHOD FOR SEPARATING PARTICLES WITHIN A SPECIMEN

FIELD OF THE INVENTION

Embodiments of the present invention relate generally to processing of biological specimens and, more particularly, to separating particles within a biological specimen for subsequent analysis.

BACKGROUND OF THE INVENTION

Various techniques have been developed to separate particles from one another. For example, using rotating disk separators for grain processing, sand and gravel sorting, and beverage sedimentation removal are well known. With respect to biological samples, centrifugal techniques have been employed. For instance, U.S. Pat. No. 6,221,655 to Fung et al. discloses a spin filter assembly for isolating and analyzing molecules and compounds present in biological and non-biological samples. In particular, Fung discloses that the spin filter may be inserted within a centrifuge holder and spun such that materials having a larger pore size than a filter at the bottom of the spin filter are retained therein. These particles may then be removed from the spin filter for further processing and analyzing. The smaller sized materials pass through the filter and collect at the bottom of the centrifuge holder and may be later discarded.

Furthermore, Ficoll® separation is a known technique that is used to separate particles within a biological sample. Generally, Ficoll® separation involves using centrifugation and density gradients to form layers of different types of particles having equivalent densities. Following separation into layers, each layer may be analyzed individually. Ficoll® separation is a slow process that may be used to separate blood into its components.

Therefore, it may be advantageous to provide a method and an apparatus for separating particles within a biological specimen. In addition, it may be advantageous to provide a method and an apparatus for collecting particles that have been separated within a biological specimen. Moreover, it may be advantageous to provide a method and an apparatus that is cost efficient and that combines several stages of processing.

SUMMARY OF THE INVENTION

Embodiments of the present invention may include an apparatus and a method for separating particles within a biological specimen. Generally, the apparatus and method provides a two-stage separation process using gravity and a disk separator. In particular, the apparatus and method may include controlling a physical state of the specimen in order to separate the particles, and then rotating the specimen in order to further separate the particles. The separated particles may be collected for further analysis. Thus, embodiments of the present invention may combine several processes for more efficient separation and analysis of a biological specimen.

According to one embodiment of the present invention an apparatus for separating particles within a biological specimen is provided. The apparatus includes a reservoir for receiving a biological specimen therein, wherein the biological specimen comprises a plurality of different sized particles in a liquid. At least one physical state of the biological specimen is capable of being controlled in order to initially separate at least a first type of particles under the influence of gravity. For example, the reservoir may be configured to receive a sample and a buffer to provide a biological specimen having a physical state that is capable of being controlled that is selected from a group consisting of density, temperature, pH, and viscosity. The apparatus also includes a rotatable disk positioned proximate to the reservoir and configured to receive at least the first type of particles thereon, wherein the rotatable disk has a plurality of holes defined therethrough that are configured to further separate at least a portion of the first type of particles based on particle size. In addition, the apparatus includes a mechanism configured to rotate the disk, and at least one collection tube positioned proximate to the rotatable disk and configured to receive at least a portion of the first type of particles passing through respective holes defined in the rotatable disk and/or around the rotatable disk in response to rotation of the disk with the mechanism.

According to various aspects of the apparatus, the rotatable disk includes a plurality of different sized holes. For instance, the rotatable disk may include a plurality of holes having a first diameter proximate to a center portion of the rotatable disk and a plurality of holes having a second diameter proximate to an outer portion of the rotatable disk. The holes of the first diameter may be smaller than the holes of the second diameter. Furthermore, the apparatus may include a plurality of collection tubes, wherein a first collection tube is configured to receive particles of the first diameter and a second collection tube is configured to receive particles of the second diameter. The apparatus may further include a third collection tube that is configured to receive particles passing around the rotatable disk. Moreover, the collection tubes may be in telescoping engagement with one another such that the third collection tube extends over the first and second collection tubes and the second collection tube extends over the first collection tube. The collection tube could also include an exit channel configured to receive a continuous collection of particles therein.

Additional aspects of the apparatus provide a rotatable disk having a magnet. The mechanism may be configured to generate a magnetic field about the rotatable disk to interact with the magnet and to thereby cause rotation of the rotatable disk. For example, the mechanism may include a magnet configured to rotate about the rotatable disk or a wire coil configured to receive an electric current therethrough. In addition, the apparatus may include a filter positioned within the reservoir that is configured such that at least the first type of particles passes through the filter before being received on the rotatable disk. The apparatus could also employ a plurality of beads that are positioned within the reservoir and that are configured to capture at least a portion of the first type of particles.

A further embodiment of the present invention provides a method for separating particles within a biological specimen. The method includes providing a biological specimen comprising a plurality of different sized particles and controlling at least one physical state of the specimen (e.g., density, temperature, pH, and viscosity) in order to separate at least a first type of particles (e.g., viruses, cells, proteins, and bacteria), such as separation under the influence of gravity. The method also includes receiving at least a portion of the first type of particles on a rotatable disk, wherein the rotatable disk has a plurality of holes defined therethrough. Moreover, the method includes rotating the disk and collecting at least a portion of the first type of particles passing through respective holes defined in the rotatable disk and/or around the rotatable disk in response to rotation of the disk so as to further separate at least a portion of the first type of particles.

Aspects of the method include controlling at least one physical state by providing a sample and a buffer in a predetermined ratio. The method could further include submerging the rotatable disk in a buffer. The method may include collecting particles within a plurality of collection tubes, wherein the collection tubes are in telescoping engagement with one another. Thus, the collection tubes may be disassembled from one another. In addition, the method may include collecting particles of different sizes within the collection tubes that each correspond to a respective particle size. The method may further include receiving a continuous collection of particles through an exit channel defined in at least one of the collection tubes. The method may include generating a magnetic field about the rotatable disk so as to interact with a magnet carried by the rotatable disk and to thereby cause rotation of the disk. The method may further include receiving at least a portion of a second type of particles on the disk separator that have been separated under the influence of gravity more slowly than the first type of particles. Furthermore, the method may include passing at least the first type of particles through a filter prior to receiving the first type of particles on the rotatable disk. The method may also include capturing at least a portion of the first type of particles with a plurality of beads prior to receiving the first type of particles on the rotatable disk.

BRIEF DESCRIPTION OF THE DRAWINGS

Figure 1:
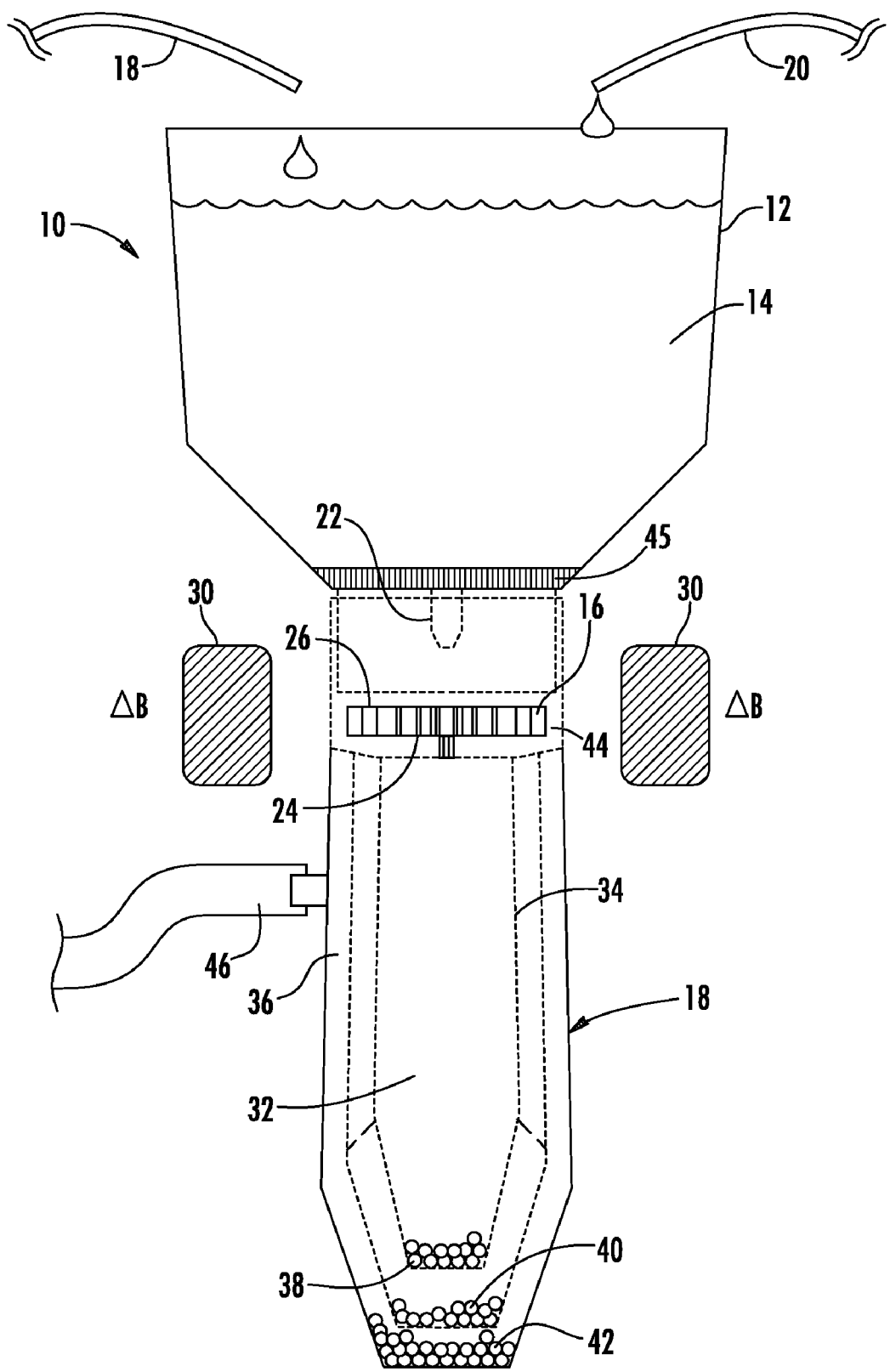
Figure 1A:
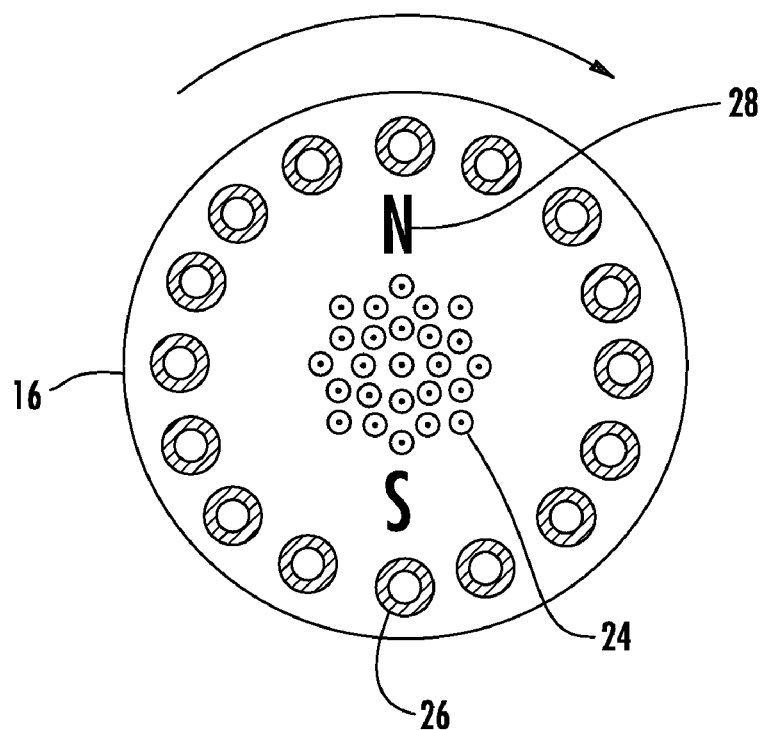
Figure 1B:
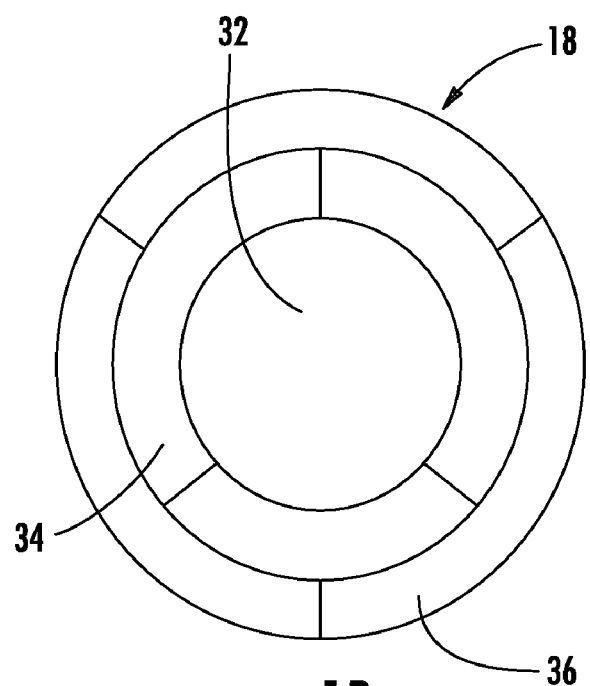

Having thus described various embodiments of the invention in general terms, reference will now be made to the accompanying drawings, which are not necessarily drawn to scale, and wherein:

FIG. 1 illustrates a cross-sectional view of an apparatus for separating and collecting particles within a biological specimen, according to one embodiment of the present invention;

FIG. 1A depicts a plan view of a disk separator according to one embodiment of the present invention; and FIG. 1B shows a plan view of a collection tube according to an embodiment of the present invention.

DETAILED DESCRIPTION

The present inventions now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Referring to FIG. 1, there is shown an apparatus 10 for separating and collecting particles within a biological specimen according to one embodiment of the present invention. In general, the apparatus 10 utilizes a two-stage separation process with a first stage separating different types of particles under the influence of gravity, and a second stage separating the particles based on particle size. More specifically, the apparatus 10 includes a mixing cup 12 for receiving a specimen 14 therein for the first stage of separation, which directs at least a portion of the specimen that has been separated onto a disk separator 16 for the second stage of separation. The disk separator 16 is rotated and particles within the specimen 14 are separated and collected within one or more collection tubes 18. Thus, the apparatus 10 is capable of combining several processes into a single apparatus for more efficient separation and/or fractionation than conventional processing.

The apparatus 10 may be employed to analyze any number of specimens, both biological and non-biological. In addition, the apparatus 10 may be used to separate and classify any number of particles within the specimen 14. For example, the particles may include any finite mass contained within a liquid specimen 14, such as cells, viruses, proteins, and the like. According to one embodiment, the apparatus 10 may be used to analyze whole blood samples by separating bacteria therefrom. Furthermore, although the term "separate" is used herein, it is understood that separation may include separation and/or fractionation of the specimen 14 in order to divide the specimen into a plurality of smaller components for subsequent analysis. Moreover, the apparatus 10 may also be used to separate a single particle type from a liquid or semi-solid specimen, which would provide concentration of the particle for further analysis. Furthermore, the apparatus 10 may also be employed to separate beads (e.g., microbeads, nanobeads, latex, polystyrene, PMMA, etc.) of various sizes that are used to capture biological or non-biological specimens. The capture techniques of the beads may be antibody, nucleic acid, biotin-streptavidin, and the like.

The mixing cup 12 may be any suitable reservoir for receiving a specimen 14 therein. As shown in FIG. 1, the mixing cup 12 may have a larger open end for receiving the specimen 14, which funnels to a smaller open end at the bottom of the mixing cup. The specimen 14 may include a raw sample 18 and may also include a buffer solution 20. The ratio of the sample 18 to the buffer solution 20 (e.g., Citrate/$H_2O$) may be regulated to provide a predetermined physical state, such as density, temperature, pH, viscosity, or the like. The predetermined physical state is selected based on characteristics of different particle types in the specimen 14 and facilitates a first stage of separation of the specimen. Thus, particles within a liquid may separate from one another as the particles settle within the mixing cup 12 under the influence of gravity. For example, the first stage of separation within the mixing cup 12 may comprise Ficoll® separation using density as the predetermined physical state. Moreover, additional techniques could be used further facilitate separation, such as vacuum, pressure, filtration, stirring, vortexing, bead capture moieties, etc. For instance, pressure could be applied over the specimen volume to further facilitate gravitational separation. According to one particular example, experimental evidence has shown that bacteria settle from a highly hypertonic solution very quickly, while blood cells will remain suspended in a septic blood sample. The settled bacterial cells remain viable and will resume their normal growth when returned to an isotonic state in media.

Different particle types that are separated within the mixing cup 12 are directed from the mixing cup onto the disk separator 16 and through sample filter 45. In particular, different types of particles may settle within the mixing cup 12 at different times based on a predetermined physical state. For instance, a first type of particle that settles quicker than other particles within the specimen 14 may pass onto the disk separator 16 before a second, third, etc. type of particles that settle slower than the first type of particles and pass to the disk separator 16 after the first type of particles or remain in the mixing cup 12. The mixing cup 12 may include a mixing cup exit 22 for directing the specimen 14 onto the center of the disk separator 16. In addition, a sample filter 45 may be used to filter the specimen 14 before being introduced to the disk separator 16.

The disk separator 16 facilitates a second type of separation of the specimen 14 that is based on particle size. In this regard, the disk separator 16 includes a plurality of holes that each extends through the thickness of the disk so as to allow at least a portion of a first type of particles that has been initially separated under the influence of gravity to travel through the holes to further separate the particles. In particular, the disk separator 16 includes a plurality of smaller holes 24 proximate to the center of the disk, and a plurality of larger holes 26 proximate to the outer edge of the disk. As shown in FIG. 1A, the smaller holes 24 may be congregated in a small cluster, while the larger holes 26 may be equidistantly spaced about the circumference of the disk separator 16.

The disk separator 16 may include a magnet 28 that is embedded or otherwise attached thereto. The magnet 28 is typically a permanent magnet having North and South magnetic poles, which facilitates rotation of the disk separator 16, as explained in further detail below. The disk separator 16 may be a polymeric material, such as polyethylene, and may further be disposable. Thus, each disk separator 16 may be used for a separate specimen 14. The disk separator 16 may have a central hole that is configured to receive a rotation spindle in the center of the collection tubes 32, 34, 36. The spindle can be deformed using heat after assembly to couple the spindle to the disk separator 16, or the spindle can be configured to fit into a hole molded into the bottom of the mixing cup 12, thus retaining the disk separator after assembly. Or, the disk separator 16 may have an axle molded to its center axis which is retained in molded hole(s) on top of the collection tubes 32, 34, 36 and/or on the bottom of the mixing cup exit 22.

A mechanism 30 is disposed proximate to the disk separator 16 for facilitating rotation of the disk. According to one embodiment where the disk separator 16 includes a magnet 28, the mechanism 30 includes at least one permanent magnet that may rotate about the apparatus 10 and proximate to the disk separator to cause rotation thereof. Thus, the mechanism 30 may include a magnet having its poles configured to attract the magnet 28 within the disk separator 16 such that rotation of the mechanism causes rotation of the disk separator. According to another aspect of the present invention, the mechanism 30 may be a wire coil that is capable of receiving an electrical current therethrough in order to create a magnetic field and facilitate rotation of the disk separator 16.

At least one collection tube 18 is positioned proximate to the disk separator 16 in order to receive particles that have been separated based on particle size. As shown in FIG. 1, there may be a plurality of collection tubes 32, 34, 36 that are each configured to receive respective particles 38, 40, 42. As such, smaller particles 38 travel through the smaller holes 24 in the disk separator 16 and into collection tube 32, and larger particles 40 travel through the larger holes 26 of the disk separator and into collection tube 34. In addition, the disk separator 16 may be positioned such that a gap 44 is located between the outer edge of the disk and the collection tube 18. The gap 44 may be sized to receive the largest particles 42, which are collected in collection tube 36.

The collection tube 18 may be coupled with the mixing cup 12. For instance, an upper portion of the collection tube 18 may extend over a lower portion of the mixing cup 12 (or vice versa), such as in a press or snap fit. Similarly, the plurality of collection tubes 32, 34, 36 may be interlocking with one another. For example, the collection tubes 32, 34, 36 may be in telescoping engagement with one another. In particular, FIG. 1B shows that collection tube 32 has the smallest diameter, collection tube 40 has a larger diameter, and collection tube 42 has the largest diameter. Thus, collection tube 40 may extend over collection tubes 32, 40, while collection tube 40 may extend over collection tube 32. The collection tubes 32, 34, 36 could interlock with a snap fit or may be partially threaded with one another such that turning one of the collection tubes with respect to another results in interlocking. Thus, the collection tubes 32, 34, 36 may be taken apart following separation for further processing of separately sized particles 38, 40, 42. Furthermore, FIG. 1 demonstrates that each of the collection tubes 32, 34, 36 may taper in order to funnel particles 38, 40, 42 from the disk separator 16 to the bottom of respective collection tubes. FIG. 1B illustrates that the collection tubes 32, 34, 36 can be held concentrically so that the spaces between the tubes remain in alignment and spacing with respect to each other and with the separation disk 16. In addition, FIG. 1B shows that partial fins 48 may be molded into the collection tubes 32, 34, 36 to provide separation clearance and spacing after assembly. In addition, each collection tube 32, 34, 36 may include an exit channel defined therein for receiving a continuous collection of particles. Thus, the exit channels may permit the collection of particles in a continuous stream. Furthermore, a vacuum may be pulled via port 46, which could be applied through the collection tubes to augment gravitational flow of the particles 38, 40, 42.

According to one embodiment of the present invention, a method for separating particles within a biological specimen 14 includes adding a sample 18 and a buffer 20 into the mixing cup 12. The ratio of the sample 18 to buffer 20 may be regulated in order to control a physical state associated with the specimen. Thus, controlling the ratio of sample 18 to buffer 20 may provide a predetermined physical state, such as density, that will allow particles within the specimen 14 to separate as the particles settle from the top of the mixing cup 12 to the bottom of the mixing cup.

Particles from mixing cup 12 that have been separated under the influence of gravity are directed onto the rotatable disk 16. The rotatable disk 16 is spun with a mechanism 30 so as to facilitate further separation of the particles based on particle size. In particular, the mechanism 30 may generate a magnetic field that interacts with a magnet 28 associated with the disk 16. As the disk 16 is rotated, particles of different sizes will be directed through holes 24, 26 defined in the disk and/or through a gap 44 defined between the disk and the collection tube 18. The collection tube 16 may include a plurality of collection tubes 32, 34, 36 for receiving different sized particles 38, 40, 42. Moreover, the collection tubes 32, 34, 36 may be separated from one another such that the particles 38, 40, 42 may be individually analyzed.

It is understood that the illustrated apparatus 10 is not meant to be limiting, as the apparatus may be various sizes and configurations in additional aspects of the present invention. For instance, the apparatus 10 may be a unitary structure that includes the mixing cup 12, disk 16, and a removably attached collection tube 18. Or, the apparatus 10 may include a mixing cup 12 that is a separate component that may be used to collect a sample 18 and that may be integrated with the disk 16 and collection tube 18, such as via a septum that may be pierced at the bottom of the mixing cup. Moreover, the holes 24, 26 may be located at any desired location on the disk 16 and may be any desired size. Moreover, the disk 16 may extend proximate to the edge of the collection tube 18 such that there is no gap 44 for receiving particles therethrough. Furthermore, there may be any number of collection tubes 32, 34, 36 depending on the amount and type of particles to be collected. In addition, although the disk 16 and collection tube 18 are shown as being generally circular in cross section, the disk and collection tube may be any desired cross section, such as rectangular or triangular.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for separating particles within a biological specimen, the apparatus comprising:
   a reservoir for receiving a biological specimen therein, wherein the biological specimen comprises a plurality of different sized particles in a liquid, and wherein at least one physical state of the biological specimen is capable of being controlled in order to initially separate at least a first type of particles under the influence of gravity;
   a rotatable disk positioned proximate to the reservoir and configured to receive at least the first type of particles thereon, wherein the rotatable disk has a plurality of different sized holes defined therethrough that are configured to further separate at least a portion of the first type of particles based on particle size;
   wherein the plurality of different sized holes comprises a plurality of holes of a first diameter proximate to a center portion of the rotatable disk and a plurality of holes of a second diameter proximate to an outer portion of the rotatable disk;
   a mechanism configured to rotate the disk;
   at least one collection tube positioned proximate to the rotatable disk and configured to receive at least a portion of the first type of particles passing through respective holes defined in the rotatable disk and/or around the rotatable disk in response to rotation of the disk with the mechanism; and
   wherein said at least one collection tube comprises a first collection tube is configured to receive particles passing through the holes of the first diameter and a second collection tube is configured to receive particles passing through the holes of the second diameter.

2. The apparatus of claim 1, wherein the plurality of holes of the first diameter are smaller than the plurality of holes of the second diameter.

3. The apparatus of claim 1, wherein a third collection tube is configured to receive at least a portion of the first type of particles passing around the rotatable disk.

4. The apparatus of claim 3, wherein the plurality of collection tubes are in telescoping engagement with one another such that the third collection tube extends over the first and second collection tubes and the second collection tube extends over the first collection tube.

5. The apparatus of claim 1, wherein the at least one collection tube comprises an exit channel configured to receive a continuous collection of particles therein.

6. The apparatus of claim 1, wherein the rotatable disk comprises a magnet.

7. The apparatus of claim 6, wherein the mechanism is configured to generate a magnetic field about the rotatable disk to interact with the magnet and to thereby cause rotation of the rotatable disk.

8. The apparatus of claim 7, wherein the mechanism comprises at least one magnet configured to rotate about the rotatable disk or a wire coil configured to receive an electric current therethrough.

9. The apparatus of claim 1, wherein the reservoir is configured to receive a sample and a buffer to provide a biological specimen having a physical state that is capable of being controlled that is selected from a group consisting of density, temperature, pH, and viscosity.

10. The apparatus of claim 1, further comprising a filter positioned within the reservoir and configured such that at least the first type of particles passes through the filter before being received on the rotatable disk.

11. The apparatus of claim 1, further comprising a plurality of beads positioned within the reservoir and configured to capture at least a portion of the first type of particles.

12. A method for separating particles within a biological specimen, the method comprising:
   providing a biological specimen comprising a plurality of different sized particles in a liquid; controlling at least one physical state of the biological specimen in order to separate at least a first type of particles; receiving at least a portion of the first type of particles on a rotatable disk, wherein the rotatable disk has a plurality of different sized holes defined therethrough;
   wherein the plurality of different sized holes comprises a plurality of holes of a first diameter proximate to a center portion of the rotatable disk and a plurality of holes of a second diameter proximate to an outer portion of the rotatable disk;
   rotating the disk;
   collecting at least a portion of the first type of particles passing through respective holes defined in the rotatable disk and/or around the rotatable disk in response to rotation of the disk so as to further separate at least a portion of the first type of particles based on particle size; and
   wherein the collecting step comprises collecting particles within a plurality of collection tubes, and wherein the plurality of collection tubes are in telescoping engagement with one another.

13. The method of claim 12, wherein the controlling step comprises providing a sample and a buffer in a predetermined ratio.

14. The method of claim 12, further comprising submerging the rotatable disk in a buffer.

15. The method of claim 12, further comprising disassembling each of the plurality of collection tubes.

16. The method of claim 12, wherein the collecting step comprises collecting particles of different sizes within the plurality of collection tubes each corresponding to a respective particle size.

17. The method of claim 12, further comprising receiving a continuous collection of particles through an exit channel defined in at least one of the plurality of collection tubes.

18. The method of claim 12, wherein the rotating step comprises generating a magnetic field about the rotatable disk so as to interact with a magnet carried by the rotatable disk.

19. The method of claim 12, wherein the controlling step comprises controlling at least one physical state of the biological specimen selected from a group consisting of density, temperature, pH, and viscosity.

20. The method of claim 12, further comprising receiving at least a portion of a second type of particles on the disk separator that have been separated under the influence of gravity more slowly than the first type of particles.

21. The method of claim 12, further comprising passing at least the first type of particles through a filter prior to receiving the first type of particles on the rotatable disk.

22. The method of claim 12, further comprising capturing at least a portion of the first type of particles with a plurality of beads prior to receiving the first type of particles on the rotatable disk.

23. The method of claim 12, wherein controlling comprises controlling the at least one physical state of the biological specimen in order to separate at least the first type of particles under the influence of gravity.

24. The method of claim 12, wherein the particles are chosen from a group consisting of viruses, cells, proteins, and bacteria.

* * * * *